(12) United States Patent
Boschetto

(10) Patent No.: US 10,973,331 B1
(45) Date of Patent: Apr. 13, 2021

(54) BACKPAIN RELIEVE SITTING DEVICES

(71) Applicant: BACK WORKS LLC, Alpharetta, GA (US)

(72) Inventor: Scott A Boschetto, Alpharetta, GA (US)

(73) Assignee: Back Works LLC, Alpharetta, GA (US)

( * ) Notice: Subject to any disclaimer, the term of this patent is extended or adjusted under 35 U.S.C. 154(b) by 0 days.

(21) Appl. No.: 17/134,480

(22) Filed: Dec. 27, 2020

(51) Int. Cl.
A47C 7/40 (2006.01)
A47C 7/42 (2006.01)
A47C 7/46 (2006.01)
A61F 5/30 (2006.01)

(52) U.S. Cl.
CPC .............. A47C 7/425 (2013.01); A47C 7/462 (2013.01); A61F 5/30 (2013.01)

(58) Field of Classification Search
CPC ............ A47C 7/425; A47C 7/462; A61F 5/30
USPC ................. 297/284.3, 284.4, 284.5
See application file for complete search history.

(56) References Cited

U.S. PATENT DOCUMENTS

| 2,060,298 A | * | 11/1936 | Gailey | A47C 7/46 |
| | | | | 297/284.5 X |
| 2,307,331 A | * | 1/1943 | Parker, Jr. | B60N 2/66 |
| | | | | 297/284.5 |
| 2,591,306 A | * | 4/1952 | Sherman | A47C 7/425 |
| | | | | 297/284.5 |
| 4,431,232 A | * | 2/1984 | Hannouche | A47C 7/425 |
| | | | | 297/284.5 |
| 4,471,993 A | * | 9/1984 | Watson | A47C 7/425 |
| | | | | 297/284.5 X |
| 4,597,386 A | * | 7/1986 | Goldstein | A61F 5/01 |
| | | | | 297/284.5 X |
| 4,824,169 A | * | 4/1989 | Jarrell | A47C 7/425 |
| | | | | 297/284.5 X |
| 4,864,668 A | * | 9/1989 | Crisp | A47C 7/021 |
| | | | | 5/653 |
| 5,039,158 A | * | 8/1991 | Maier | A47C 7/425 |
| | | | | 297/452.37 |

(Continued)

FOREIGN PATENT DOCUMENTS

WO     WO-02080734 A1 * 10/2002 ............... A47C 7/46

Primary Examiner — Rodney B White
(74) Attorney, Agent, or Firm — Ming Jiang; MM IP Services LLC

(57) ABSTRACT

Certain aspects of present disclosure relate to single-side and dual-side backpain relieve sitting devices. In certain embodiment, single-side backpain relieve sitting device includes a rectangular baseplate, a backpain relieve cushion support mounted on the rectangular baseplate, a backpain relieve cushion formed on a top end of backpain relieve cushion support. A dual side backpain relieve sitting device is constructed placing one single-side backpain relieve sitting device on one side of the rectangular baseplate, and another symmetric single-side backpain relieve sitting device on other side of the rectangular baseplate. The backpain relieve sitting device is removably and vertically mounted on a chair. The backpain relieve cushions is used to press two corresponding posterior superior iliac spines and to prevent counterclockwise rotary posterior pelvic tilt more than 90 degrees to a neutral and intuitive Lumbar lordotic angle while in a sitting position without compression over the spinous processes of the sacrum.

20 Claims, 9 Drawing Sheets

(56) References Cited

U.S. PATENT DOCUMENTS

| | | | | |
|---|---|---|---|---|
| 5,456,519 | A * | 10/1995 | Davis | A47C 7/425 |
| | | | | 297/219.1 X |
| 5,685,613 | A * | 11/1997 | Franzen, Jr. | A47G 9/10 |
| | | | | 297/284.5 X |
| 5,711,575 | A * | 1/1998 | Hand | A47C 7/425 |
| | | | | 297/284.5 X |
| 5,863,095 | A * | 1/1999 | Rivard | A47C 7/46 |
| | | | | 297/284.5 X |
| 6,125,851 | A * | 10/2000 | Walker | A61G 5/1091 |
| | | | | 128/845 |
| 6,206,463 | B1 * | 3/2001 | Whigham | A47C 4/52 |
| | | | | 297/284.5 X |
| 8,398,170 | B2 * | 3/2013 | Walker | A47C 7/14 |
| | | | | 297/284.4 X |
| 8,740,303 | B2 * | 6/2014 | Halliday | A47C 31/126 |
| | | | | 297/284.3 |
| 2005/0121957 | A1 * | 6/2005 | Matsushima | A47C 31/126 |
| | | | | 297/284.5 |
| 2006/0097556 | A1 * | 5/2006 | Jang | A47C 7/46 |
| | | | | 297/284.4 |
| 2012/0306247 | A1 * | 12/2012 | Bisman | A47C 7/462 |
| | | | | 297/284.4 X |
| 2013/0001993 | A1 * | 1/2013 | Kurata | A47C 7/462 |
| | | | | 297/284.4 |
| 2013/0226053 | A1 * | 8/2013 | Khan | B60N 2/666 |
| | | | | 601/134 |
| 2013/0312195 | A1 * | 11/2013 | Berube | A47C 7/425 |
| | | | | 5/648 |
| 2015/0182027 | A1 * | 7/2015 | Chang | A47C 9/002 |
| | | | | 297/344.1 |
| 2018/0027971 | A1 * | 2/2018 | St. Mary | A47C 9/005 |
| 2019/0274861 | A1 * | 9/2019 | Gitomer | A41D 23/00 |
| 2020/0093271 | A1 * | 3/2020 | Kopperud | A47C 7/465 |

* cited by examiner

BACKPAIN RELIEVE SITTING DEVICES

FIELD

The present disclosure generally relates to the field of sitting devices, and more particularly to single-side backpain relieve sitting devices and dual-side backpain relieve sitting devices.

BACKGROUND

The background description provided herein is for the purpose of generally presenting the context of the present disclosure. Work of the presently named inventors, to the extent it is described in this background section, as well as aspects of the description that may not otherwise qualify as prior art at the time of filing, are neither expressly nor impliedly admitted as prior art against the present disclosure.

There is a long-felt but unresolved need in the medical industry to address the most important issue of back pain in sitting, that is duration. Lumbar supports are shown to impact the vertebral motions of the lumbar spine and increasing lumbar support results in increased radiographic lumbar lordosis yet had no effect on pelvic postures. Therefore, there is huge potential for increased strains at the lumbosacropelvic junction, the origin of all back issues. Sitting involves a flexed spine posture of up to about 97% of end range of motion. When Lumbosacral joint moves away from neutral and toward end range, the tissues surrounding this, and contiguous lumbar joints are subject to increasing levels of stress and strain triggering pain signals from the mechanical pain sensors in these tissues. Most people who have back pain are told they have one of most five common diagnosis, spinal stenosis, arthritis, degenerative disc disease, herniated disc and muscle strain. The common theme that gives rise to one of the five diagnoses is constant low-level strain causing wear and tear over time.

The other problem in this industry is that most lumbar supports do not address isolated pelvic support in sitting. The indoctrination of sitting posture as a causative factor by health professionals and writers of medical literature is prevalent. Truth being posture is not important to the minds of the consumers, but pain is. Adhering to the science and biomechanical analysis of the functionality of spine at the lumbosacropelvic region is most important and most complex to diagnose. There needs to be a device that supports the pelvis in sitting in an isolated fashion and allows the user to experience a natural pain free postural response.

Therefore, an unaddressed need exists in the art to address the aforementioned deficiencies and inadequacies.

SUMMARY

In one aspect, present disclosure relates to a single-side backpain relieve sitting device. In certain embodiments, the single-side backpain relieve sitting device includes: a rectangular baseplate, a backpain relieve cushion support, and a backpain relieve cushion. In certain embodiments, the rectangular baseplate includes: a first edge, a second edge, a third edge, and a fourth edge. The backpain relieve cushion support includes: a first side, a second side, a third side, and a fourth side. In certain embodiments, each of the four sides of the backpain relieve cushion support is in a trapezoid shape, and each of the four sides includes a bottom end and a top end. A depth D1 of the backpain relieve cushion support is approximately 2.0 to 6.5 inches. The backpain relieve cushion is formed at the top ends of the four sides of the backpain relieve cushion support.

In certain embodiments, the backpain relieve cushion support is removably attached to the rectangular baseplate. Each of the bottom end of the four sides of the backpain relieve cushion support is aligned with a corresponding edge of the rectangular baseplate. Each top end of the four sides of the backpain relieve cushion support converges at the top ends of the four sides of the backpain relieve cushion support to form the backpain relieve cushion. The backpain relieve cushion is used to press one of two posterior superior iliac spines and to prevent counterclockwise rotary posterior pelvic tilt more than 90 degrees to a neutral and intuitive Lumbar lordotic angle while in a sitting position without compression over the spinous processes of the sacrum.

In certain embodiments, the backpain relieve sitting device is removably and vertically mounted on a chair such that the first edge of the rectangular baseplate is aligned with a spine of a person sitting on the chair. The rectangular baseplate is a rigid board, and the rectangular baseplate includes four rounded corners. The rectangular baseplate is approximately six inches in height and six inches in width.

In certain embodiments, the backpain relieve cushion is made of a pressable soft material to prevent counterclockwise rotary posterior pelvic tilt more than 90 degrees. A vertical distance H1 between a center of the backpain relieve cushion and the fourth edge of the rectangular baseplate is approximately 3.0 to 5.0 inches. A lateral distance L1 between a center of the backpain relieve cushion and the first edge of the rectangular baseplate is approximately 1.5 to 3.0 inches.

In certain embodiments, the backpain relieve cushion is in a parallelogram shape. The parallelogram is shaped to descend from the third side to the second side of the backpain relieve cushion support to accommodate variations of distance between two posterior superior iliac spines among children, adults, males and females.

In another aspect, the present disclosure relates to a dual-side backpain relieve sitting device. In certain embodiments, the dual-side backpain relieve sitting device includes: a rectangular baseplate, a pair of backpain relieve cushion supports, and a pair of backpain relieve cushions.

In certain embodiments, the rectangular baseplate includes: a first edge, a second edge, a third edge, a fourth edge, and a center line between the second edge and the fourth edge. The pair of backpain relieve cushion supports includes a first backpain relieve cushion support and a second backpain relieve cushion support. The first backpain relieve cushion support includes: a first side, a second side, a third side, and a fourth side. The second backpain relieve cushion support includes: a first side, a second side, a third side, and a fourth side. Each of the four sides of the pair of backpain relieve cushions is in a trapezoid shape. A depth D2 of the backpain relieve cushion supports is approximately 2.0 to 6.5 inches. Each of the four sides includes a bottom end and a top end.

In certain embodiments, the pair of backpain relieve cushions includes a first backpain relieve cushion and a second backpain relieve cushion. Each of the first backpain relieve cushion and the second backpain relieve cushion is formed at the corresponding top ends of the four sides of the pair of backpain relieve cushion supports.

In certain embodiments, the pair of backpain relieve cushion supports is removably attached side-by-side to the rectangular baseplate, the bottom end of the third side of the first backpain relieve cushion support connects the bottom end of the second side of the second backpain relieve cushion support through a space along the center line to form a valley of non-contact space. Each top end of the four sides of the first backpain relieve cushion support converges to form the first backpain relieve cushion and each top end of the four sides of the second backpain relieve cushion support converges to form the second backpain relieve cushion, respectively. The pair of the backpain relieve cushions is used to press two corresponding posterior superior iliac spines and to prevent counterclockwise rotary posterior pelvic tilt more than 90 degrees to a neutral and intuitive Lumbar lordotic angle while in a sitting position without compression over the spinous processes of the sacrum.

In certain embodiments, the dual-side backpain relieve sitting device is removably and vertically mounted on a chair such that the center line of the rectangular baseplate is aligned with a spine of a person sitting on the chair.

In certain embodiments, the rectangular baseplate is made of a rigid board and the rectangular baseplate includes four rounded corners. The rectangular baseplate is approximately 6 inches in height and 12 inches in width.

In certain embodiments, each of the pair of backpain relieve cushions is made of a pressable soft material to prevent counterclockwise rotary posterior pelvic tilt more than 90 degrees. A distance between the centers of the first backpain relieve cushion and the second backpain relieve cushion is approximately 3.0 inches to 5.0 inches. A vertical distance H2 between a center of the first backpain relieve cushion and the third edge of the rectangular baseplate and another vertical distance H2 between a center of the second backpain relieve cushion and the third edge of the rectangular baseplate are approximately about 3.0 to 5.0 inches.

In certain embodiments, each of the pair of backpain relieve cushions is in a parallelogram shape. The parallelogram of the first backpain relieve cushion is shaped to descend from the second side towards the third side of the first backpain relieve cushion support, and the parallelogram of the second backpain relieve cushion is shaped to descend from the second side towards the third side of the second backpain relieve cushion support to accommodate variations of distance between two posterior superior iliac spines among children, adults, males and females.

These and other aspects of the present disclosure will become apparent from the following description of the preferred embodiment taken in conjunction with the following drawings, although variations and modifications therein may be effected without departing from the spirit and scope of the novel concepts of the present disclosure.

BRIEF DESCRIPTION OF THE DRAWINGS

The accompanying drawings illustrate one or more embodiments of the present disclosure and, together with the written description, serve to explain the principles of the present disclosure. Wherever possible, the same reference numbers are used throughout the drawings to refer to the same or like elements of an embodiment. The drawings do not limit the present disclosure to the specific embodiments disclosed and described herein. The drawings are not necessarily to scale, emphasis instead being placed upon clearly illustrating the principles of the present disclosure, and wherein.

DETAILED DESCRIPTION

Figure 1:
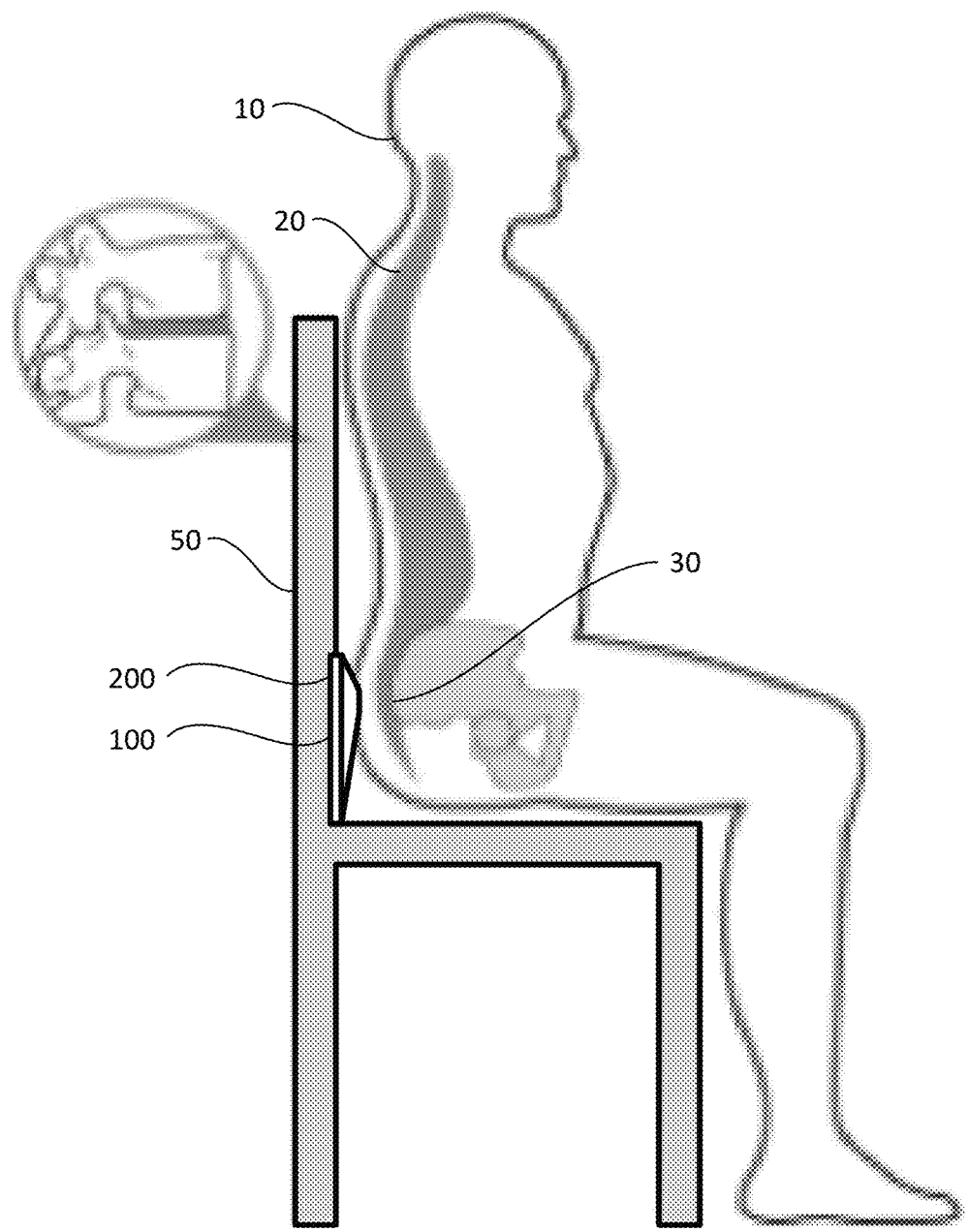
FIG. 1 illustrates a person sitting on a chair using a backpain relieve sitting device according to certain embodiments of the present disclosure.

The present disclosure will now be described more fully hereinafter with reference to the accompanying drawings, in which exemplary embodiments of the present disclosure are shown. This present disclosure may, however, be embodied in many different forms and should not be construed as limited to the embodiments set forth herein. Rather, these embodiments are provided so that this present disclosure will be thorough and complete, and will fully convey the scope of the present disclosure to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," or "includes" and/or "including" or "has" and/or "having" when used herein, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom", "upper" or "top," and "front" or "back" may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this present disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximates, meaning that the term "around", "about" or "approximately" can be inferred if not expressly stated.

Many specific details are provided in the following descriptions to make the present disclosure be fully understood, but the present disclosure may also be implemented by using other manners different from those described herein, so that the present disclosure is not limited by the specific embodiments disclosed in the following.

The description will be made as to the embodiments of the present disclosure in conjunction with the accompanying drawings FIGS. 1 through 9. In accordance with the purposes of this present disclosure, as embodied and broadly described and shown in FIGS. 1 and 5, herein, this present disclosure, in one aspect, relates to a single-side backpain relieve sitting device 100. In certain embodiments, the single-side backpain relieve sitting device 100 includes: a rectangular baseplate 130, a backpain relieve cushion support 120, and a backpain relieve cushion 110.

Figure 5:
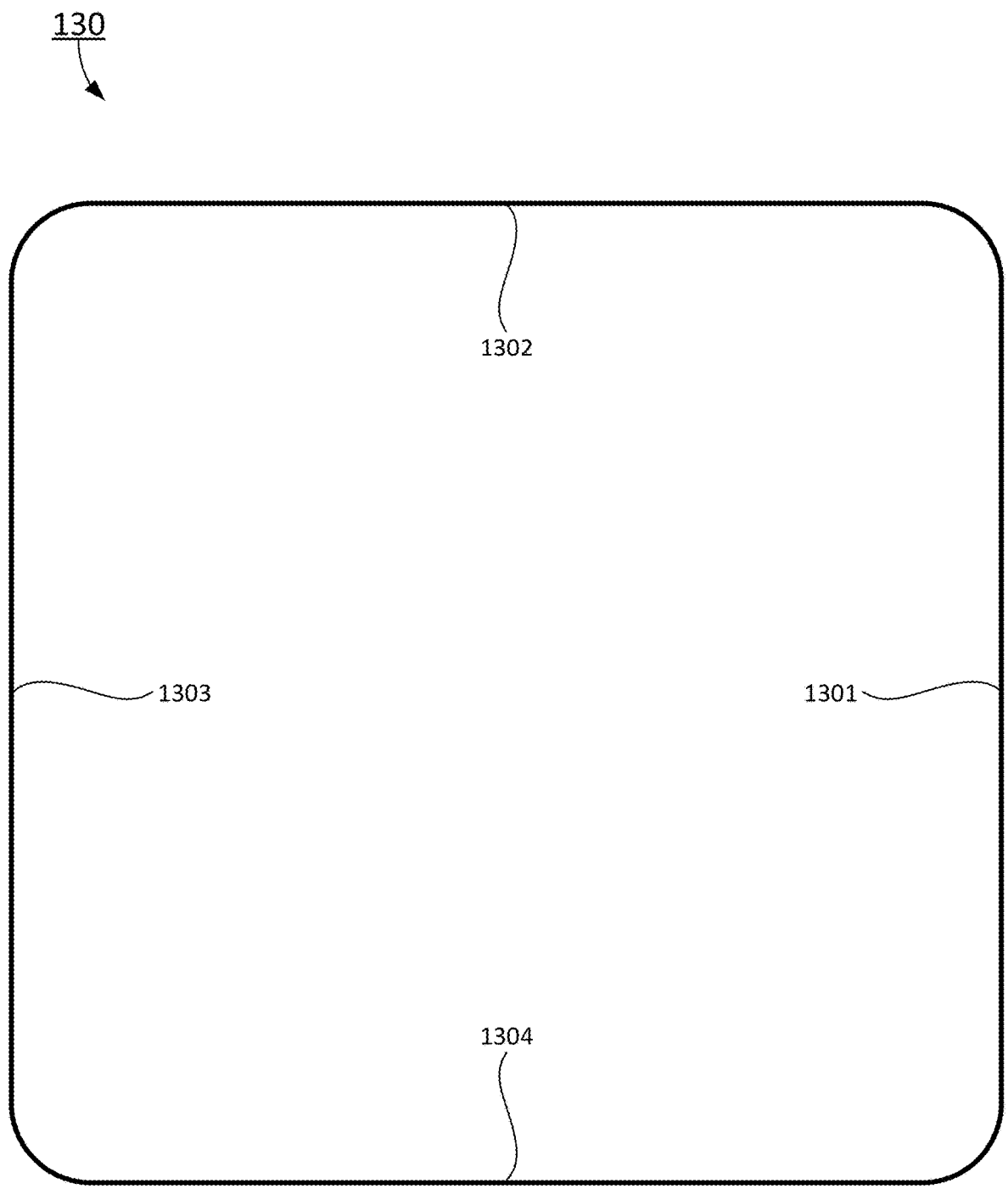
FIG. 5 is front view of a rectangular backplate of the single-side backpain relieve sitting device according to certain embodiments of the present disclosure.
Figure 6:
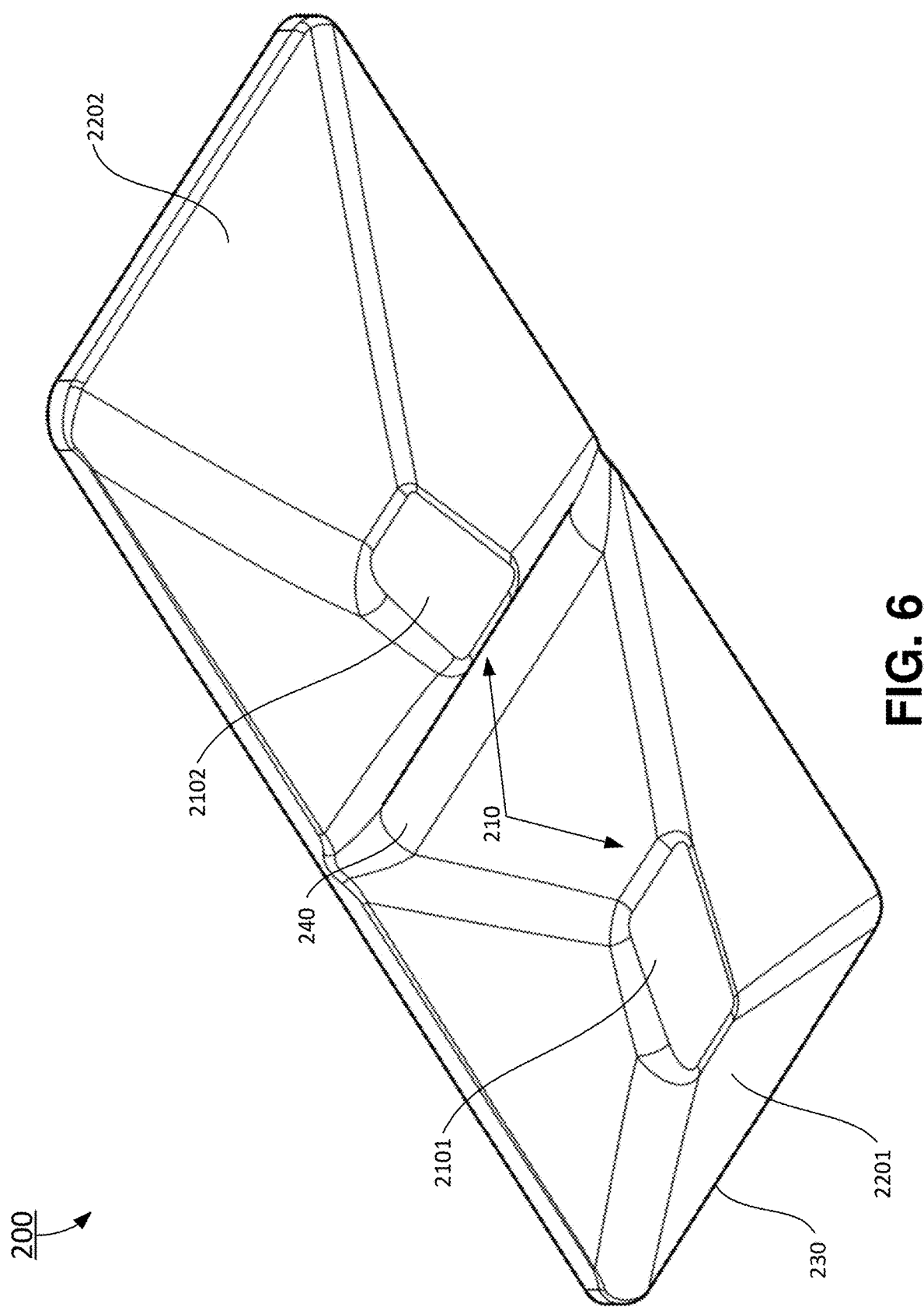
FIG. 6 is an upper left perspective view of a dual-side backpain relieve sitting device according to certain embodiments of the present disclosure.

In certain embodiments, as shown in FIG. 5, the rectangular baseplate 130 includes: a first edge 1301, a second edge 1302, a third edge 1303, and a fourth edge 1304. The rectangular baseplate 130 is a rigid board to maintain the backpain relieve cushion support 120 and the backpain relieve cushion 110 in their relative position when the single-side backpain relieve sitting device 100 is mounted in a chair 50, as shown in FIG. 1. The rectangular baseplate 130 includes four rounded corners to ensure smooth transitions around four corners. In one embodiment, the rectangular baseplate 130 is approximately six inches in height and six inches in width.

Figure 3:
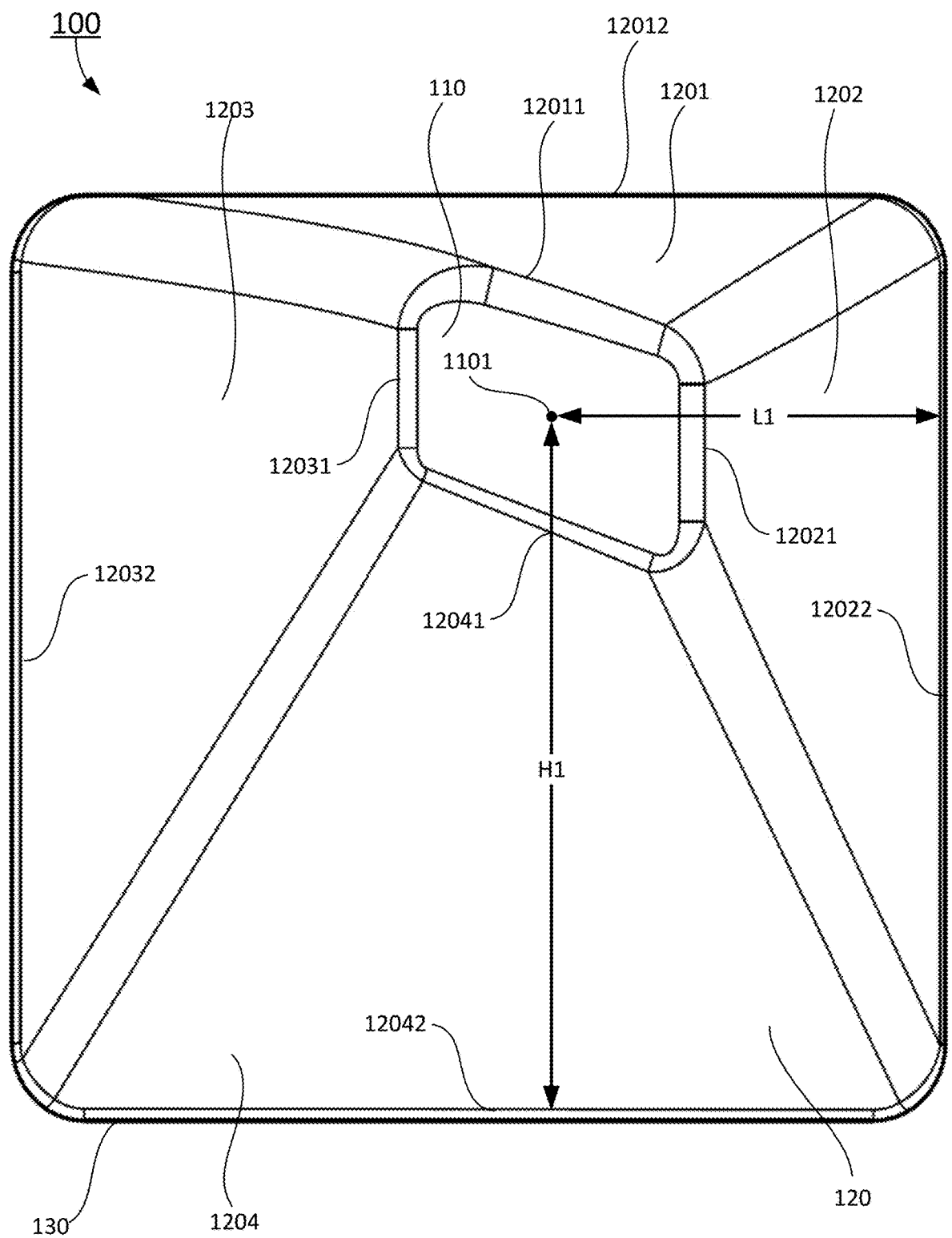
FIG. 3 is a front view of the single-side backpain relieve sitting device according to certain embodiments of the present disclosure.
Figure 4:
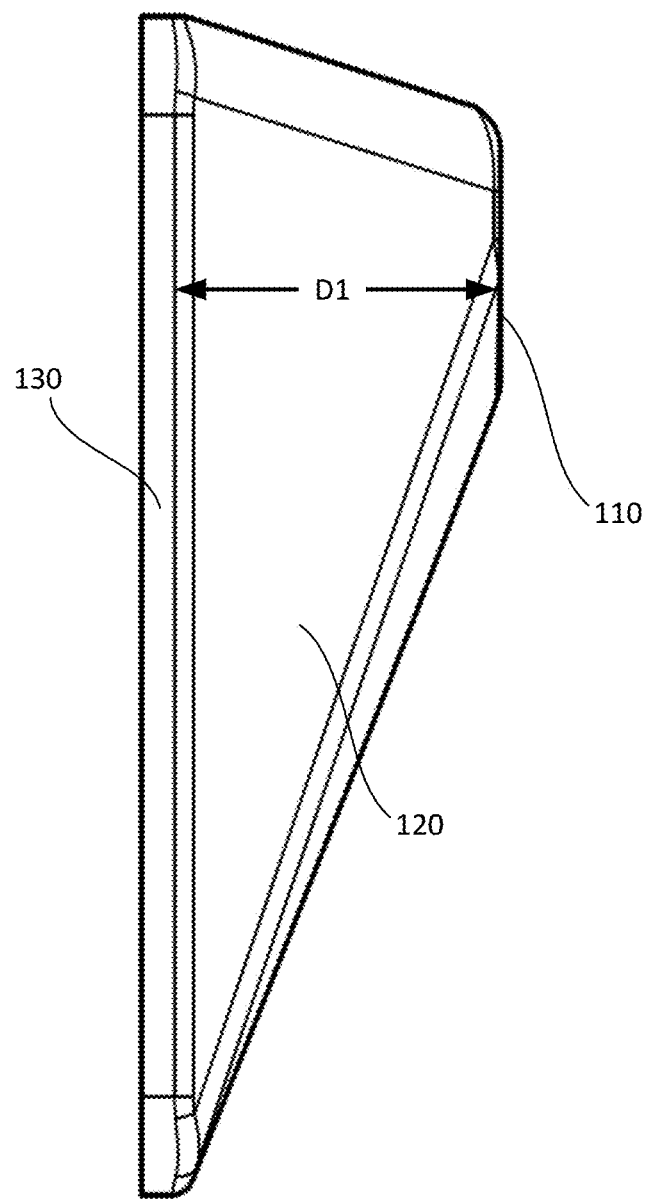
FIG. 4 is a side view of single-side backpain relieve sitting device according to certain embodiments of the present disclosure.

In certain embodiments, as shown in FIG. 3, the backpain relieve cushion support 120 includes: a first side 1201, a second side 1202, a third side 1203, and a fourth side 1204. In certain embodiments, each of the four sides of the backpain relieve cushion support 120 is in a trapezoid shape. A depth D1 of the backpain relieve cushion support is approximately 2.0 to 6.5 inches, as shown in FIG. 4. The depth D1 varies depending on the chair where the single-side backpain relieve sitting device 100 is mounted. In one embodiment, for a straight up chair, the depth D1 is approximately 2.0 to 3.75 inches. In another embodiment, for a soft surface sofa, the depth D1 is approximately 4.0 to 6.5 inches. Each of the four sides includes a bottom end and a top end. The first side 1201 of the backpain relieve cushion support 120 includes a top end 12011 and a bottom end 12012. The second side 1202 of the backpain relieve cushion support 120 includes a top end 12021 and a bottom end 12022. The third side 1203 of the backpain relieve cushion support 120 includes a top end 12031 and a bottom end 12032. The fourth side 1204 of the backpain relieve cushion support 120 includes a top end 12041 and a bottom end 12042. The backpain relieve cushion 110 is formed at the top ends 12011, 12012, 12013, and 12014 of the four sides 1201, 1202, 1203, and 1204 of the backpain relieve cushion support 120.

In certain embodiments, the backpain relieve sitting device 100 is removably and vertically mounted on a chair 50 such that the first edge 1301 of the rectangular baseplate 130 is aligned with a spine of a person 10 sitting on the chair 50. In one embodiment, the rectangular baseplate 130 is a rigid board, and the rectangular baseplate 130 includes four rounded corners. The rectangular baseplate 130 is approximately six inches in height and six inches in width.

In certain embodiments, the backpain relieve cushion 110 is made of a pressable soft material to prevent counterclockwise rotary posterior pelvic tilt more than 90 degrees. A vertical distance H1 between a center 1101 of the backpain relieve cushion 110 and the fourth edge 1304 of the rectangular baseplate 130 is approximately 3.0 to 5.0 inches. A lateral distance L1 between the center 1101 of the backpain relieve cushion 110 and the first edge 1301 of the rectangular baseplate 130 is approximately 1.5 to 3.0 inches.

Figure 2:
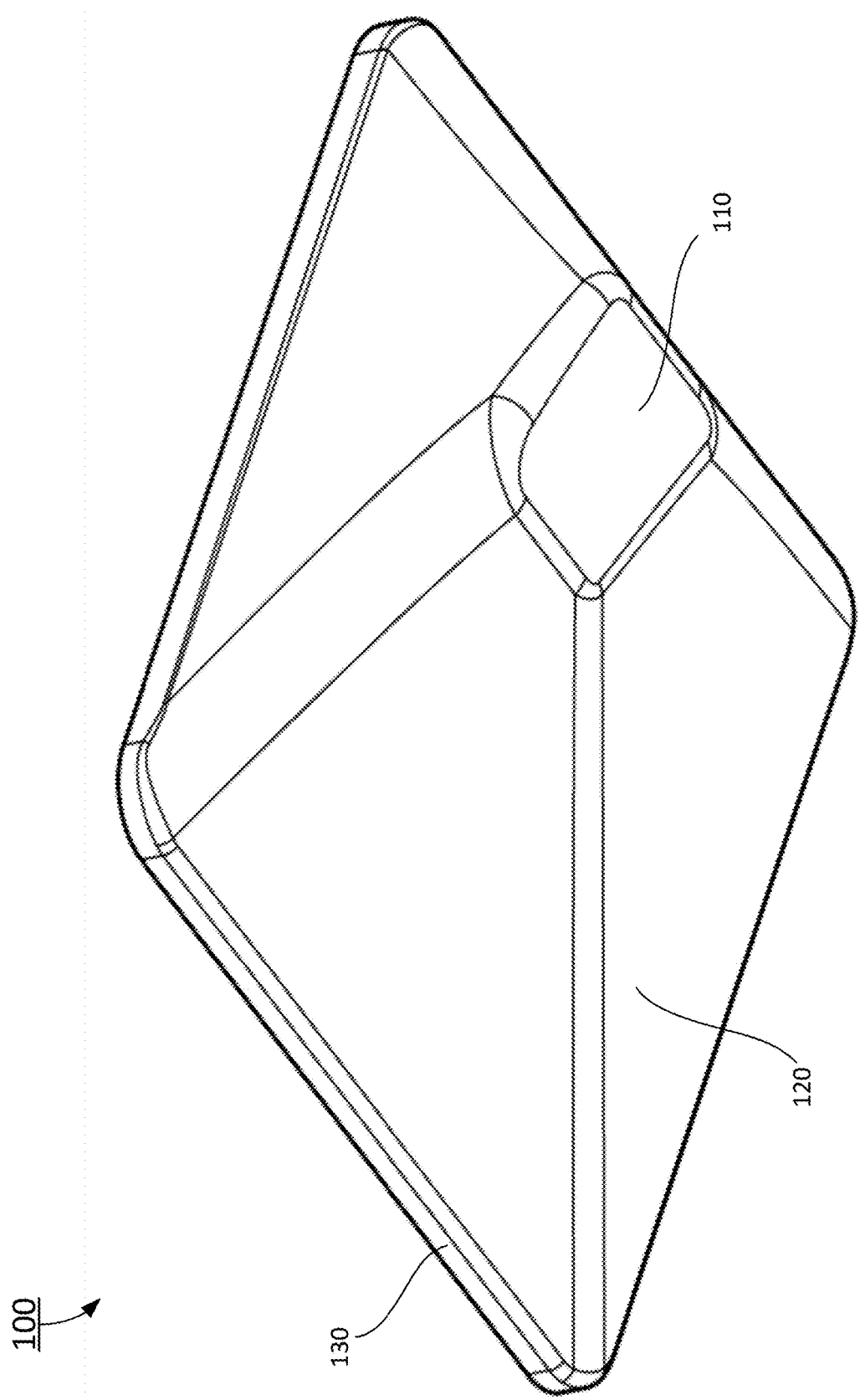
FIG. 2 is an upper left perspective view of a single-side backpain relieve sitting device according to certain embodiments of the present disclosure.

In certain embodiments, as shown in FIGS. 2 and 3, the backpain relieve cushion 110 is in a parallelogram shape. The parallelogram is shaped to descend from the third side 1203 to the second side 1202 of the backpain relieve cushion support 120 to accommodate variations of distance between two posterior superior iliac spines 30 among children, adults, males and females.

In certain embodiments, the backpain relieve cushion support 120 is removably attached to the rectangular baseplate 130. Each of the bottom end of the four sides of the backpain relieve cushion support 120 is aligned with a corresponding edge of the rectangular baseplate 130. As shown in FIGS. 2 and 3, the bottom end 12012 of the first side 1201 of the backpain relieve cushion support 120 meets the first edge 1301 of the rectangular baseplate 130. The bottom end 12022 of the second side 1202 of the backpain relieve cushion support 120 meets the second edge 1303 of the rectangular baseplate 130. The bottom end 12032 of the third side 1203 of the backpain relieve cushion support 120 meets the third edge 1303 of the rectangular baseplate 130. The bottom end 12042 of the fourth side 1204 of the backpain relieve cushion support 120 meets the fourth edge 1304 of the rectangular baseplate 130. The top ends 12011, 12012, 12013, and 12014 of the four sides 1201, 1202, 1203, and 1204 of the backpain relieve cushion support 120 converges at the top ends of the four sides of the backpain relieve cushion support 120 to form the backpain relieve cushion 110. The backpain relieve cushion 110 is used to press one of two posterior superior iliac spines 30 and to prevent counterclockwise rotary posterior pelvic tilt more than 90 degrees to a neutral and intuitive Lumbar lordotic angle while in a sitting position without compression over the spinous processes of the sacrum. Therefore, the backpain caused by the compression over the spinous processes of the sacrum and the compression of the discs of the spine 20 is relieved. This backpain relieve method differs from the application of lumbar support. Most lumbar support are placed in the back of the spine and the backpain relieve cushion 110 is placed around pelvis to press one of the two posterior superior iliac spines 30 of the person 10.

In certain embodiments, as shown in FIGS. 2 and 3, the single-side backpain relieve sitting device 100 is used for the person 10 in the lower right hand side of his/her pelvis. Alternative embodiments such as a single-side backpain relieve sitting device having a mirror image of the single-side backpain relieve sitting device 100 will become apparent to those skilled in the art to which the present disclosure pertains without departing from its spirit and scope.

In another aspect, the present disclosure relates to a dual-side backpain relieve sitting device 200, as shown in FIGS. 1, 6, 7, 8 and 9. In certain embodiments, the dual-side backpain relieve sitting device 200 includes: a rectangular baseplate 230, a pair of backpain relieve cushion supports 220, and a pair of backpain relieve cushions 210.

Figure 9:
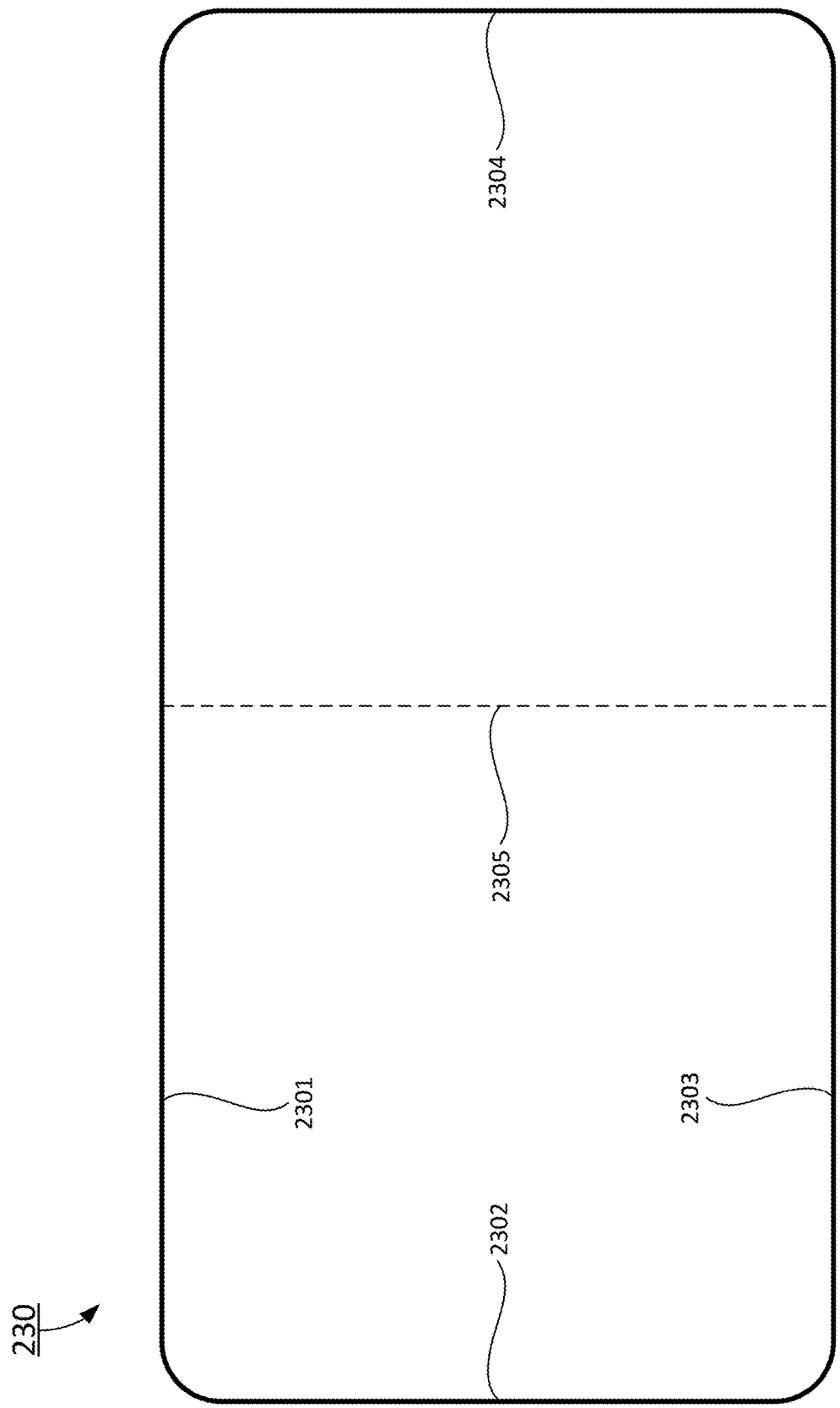
FIG. 9 is front view of a rectangular backplate of the dual-side backpain relieve sitting device according to certain embodiments of the present disclosure.

In certain embodiments, as shown in FIG. 9, the rectangular baseplate 230 includes: a first edge 2301, a second edge 2302, a third edge 2303, a fourth edge 2304, and a center line 2305 between the second edge 2302 and the fourth edge 2304.

Figure 7:
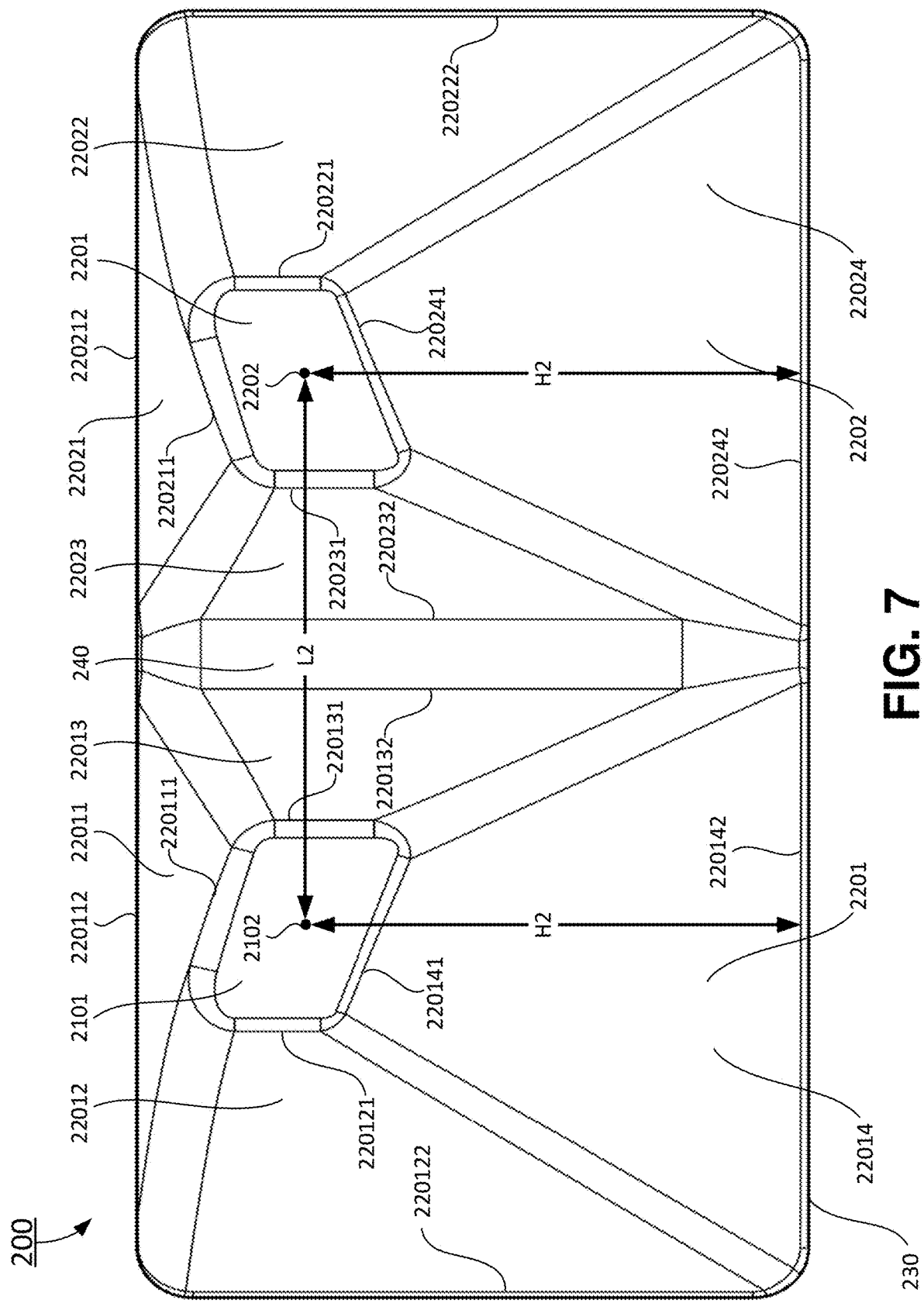
FIG. 7 is a front view of the dual-side backpain relieve sitting device according to certain embodiments of the present disclosure.
Figure 8:
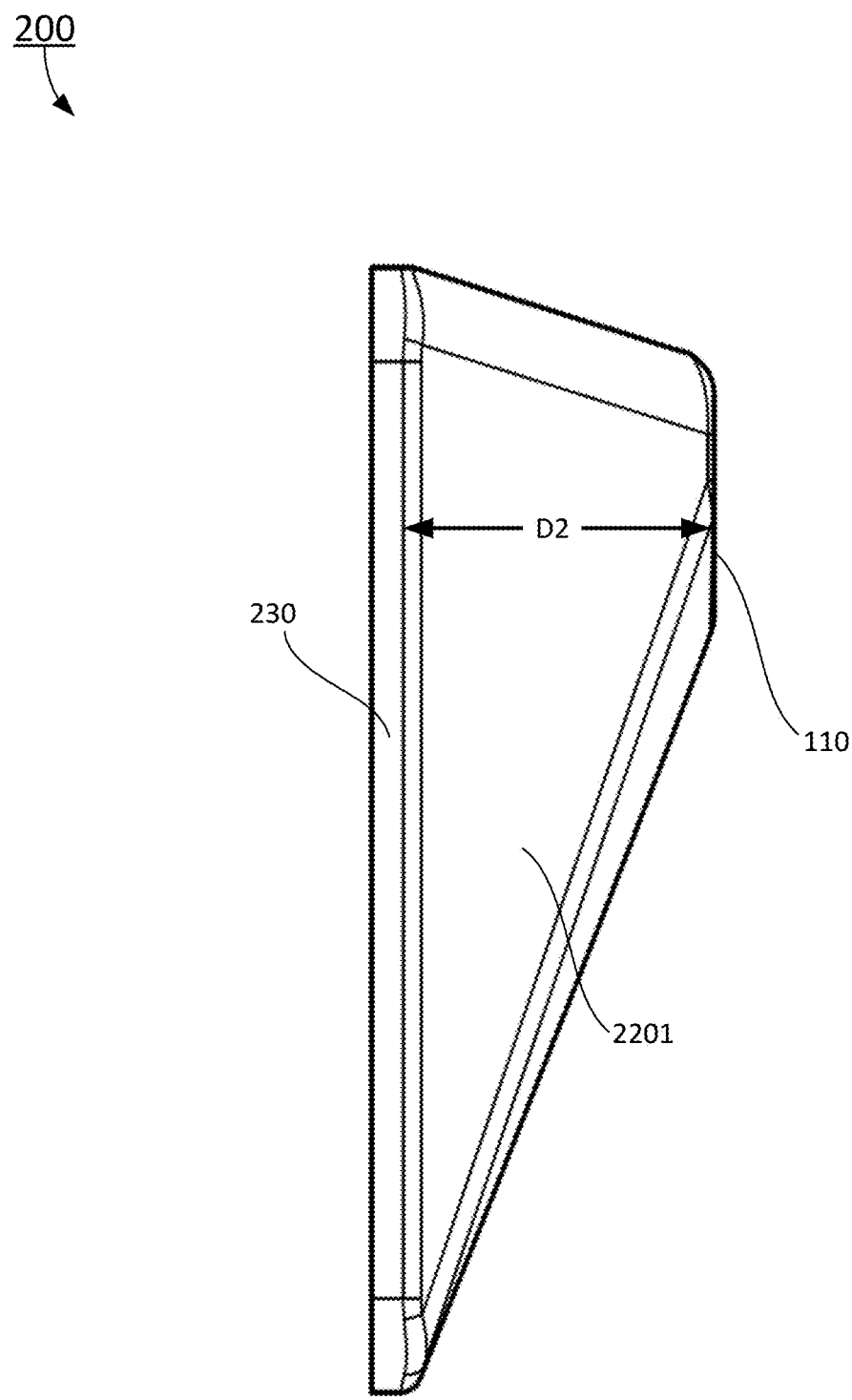
FIG. 8 is a side view of dual-side backpain relieve sitting device according to certain embodiments of the present disclosure.

In certain embodiments, as shown in FIG. 7, the pair of backpain relieve cushion supports 220 includes a first backpain relieve cushion support 2201 and a second backpain relieve cushion support 2202. The first backpain relieve cushion support 2201 includes: a first side 22011, a second side 22012, a third side 22013, and a fourth side 22014. The second backpain relieve cushion support 2202 includes: a first side 22021, a second side 22022, a third side 22023, and a fourth side 22024. Each of the first side 22011, the second side 22012, the third side 22013, and the fourth side 22014 of the first backpain relieve cushion support 2201, and each of the first side 22021, the second side 22022, the third side 22023, and the fourth side 22024 of the second backpain relieve cushion support 2202 is in a trapezoid shape. A depth D2 of the backpain relieve cushion supports is approximately 2.0 to 6.5 inches, as shown in FIG. 8. The depth D2 varies depending on the chair where the dual-side backpain relieve sitting device 200 is mounted. In one embodiment, for a straight up chair, the depth D2 is approximately 2.0 to 3.75 inches. In another embodiment, for a soft surface sofa, the depth D2 is approximately 4.0 to 6.5 inches.

In certain embodiments, as shown in FIG. 7, the first side 22011 of the first backpain relieve cushion support 2201 includes a top end 220111 and a bottom end 220112. The second side 22012 of the first backpain relieve cushion support 2201 includes a top end 220121 and a bottom end 220122. The third side 22013 of the first backpain relieve cushion support 2201 includes a top end 220131 and a bottom end 220132. The fourth side 22014 of the first backpain relieve cushion support 2201 includes a top end 220141 and a bottom end 220142. The first side 22021 of the second backpain relieve cushion support 2202 includes a top end 220211 and a bottom end 220212. The second side 22012 of the second backpain relieve cushion support 2202 includes a top end 220221 and a bottom end 220222. The third side 22013 of the second backpain relieve cushion support 2202 includes a top end 220231 and a bottom end 220232. The fourth side 22014 of the second backpain relieve cushion support 2202 includes a top end 220241 and a bottom end 220242.

In certain embodiments, as shown in FIG. 7, the pair of backpain relieve cushions 210 includes a first backpain relieve cushion 2101 and a second backpain relieve cushion 2102. The first backpain relieve cushion 2101 is formed at the corresponding the top end 220111 of the first side 22011, the top end 220121 of the second side 22012, the top end 220131 of the third side 22013, and the top end 220141 of the fourth side 22014 of the first backpain relieve cushion support 2201. The second backpain relieve cushion 2102 is formed at the corresponding top end 220121 of the first side 22012, top end 220221 of the second side 22022, the top end 220231 of the third side 22023, and the top end 220241 of the fourth side 22024 of the second backpain relieve cushion support 2202.

In certain embodiments, the pair of backpain relieve cushion supports 220 is removably attached side-by-side to the rectangular baseplate 230, the bottom end 220132 of the third side 22013 of the first backpain relieve cushion support 2201 connects the bottom end 220232 of the second side 22023 of the second backpain relieve cushion support 2202 through a space 240 along the center line 2305 to form a valley of non-contact space. The top end 220111 of the first side 22011, the top end 220121 of the second side 22012, the top end 220131 of the third side 22013, and the top end 220141 of the fourth side 22014 of the first backpain relieve cushion support 2201 converges to form the first backpain relieve cushion 2101, and the top end 220121 of the first side 22012, top end 220221 of the second side 22022, the top end 220231 of the third side 22023, and the top end 220241 of the fourth side 22024 of the second backpain relieve cushion support 2202 converges to form the second backpain relieve cushion 2102, respectively. The pair of the backpain relieve cushions 210 is used to press two corresponding posterior superior iliac spines 30 of a person 10 sitting in a chair 50 and to prevent counterclockwise rotary posterior pelvic tilt more than 90 degrees to a neutral and intuitive Lumbar lordotic angle while in a sitting position without compression over the spinous processes of the sacrum. Therefore, the backpain caused by the compression over the spinous processes of the sacrum and the compression of the discs of the spine 20 is relieved. This backpain relieve method differs from the application of lumbar support. Most lumbar support are placed in the back of the spine and the pair of the backpain relieve cushions 210 is placed around pelvis to press two corresponding posterior superior iliac spines 30 of the person 10.

In certain embodiments, as shown in FIG. 1, the dual-side backpain relieve sitting device 200 is removably and vertically mounted on a chair 50 such that the center line 2305 of the rectangular baseplate 230 is aligned with a spine 20 of the person 10 sitting on the chair 50.

In certain embodiments, the rectangular baseplate 230 is made of a rigid board and the rectangular baseplate 230 includes four rounded corners. In one embodiment, the rectangular baseplate 130 is approximately 6 inches in height and 12 inches in width.

In certain embodiments, each of the pair of backpain relieve cushions 210 is made of a pressable soft material to prevent counterclockwise rotary posterior pelvic tilt more than 90 degrees. In certain embodiments, a lateral distance L2 between a center 2102 of the first backpain relieve cushion 2101 and a center 2202 of the second backpain relieve cushion 2102 is approximately 3.0 to 5.0 inches. In certain embodiments, a vertical distance H2 between the center 2102 of the first backpain relieve cushion 2101 and the third edge 2303 of the rectangular baseplate 230 and another vertical distance H2 between the center 2202 of the second backpain relieve cushion 2102 and the third edge 2303 of the rectangular baseplate 230 are approximately about 3.0 to 5.0 inches.

In certain embodiments, each of the pair of backpain relieve cushions 210 is in a parallelogram shape. The parallelogram of the first backpain relieve cushion 2101 is shaped to descend from the second side 22012 towards the third side 22013 of the first backpain relieve cushion support 2201, and the parallelogram of the second backpain relieve cushion 2102 is shaped to descend from the second side 22022 towards the third side 22023 of the second backpain relieve cushion support 2202 to accommodate variations of distance between two posterior superior iliac spines 30 among children, adults, males and females.

The foregoing description of the exemplary embodiments of the present disclosure has been presented only for the purposes of illustration and description and is not intended to be exhaustive or to limit the present disclosure to the precise forms disclosed. Many modifications and variations are possible in light of the above teaching. The embodiments were chosen and described in order to explain the principles of the present disclosure and their practical application so as to activate others skilled in the art to utilize the present disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims, the foregoing description and the exemplary embodiments described therein, and accompanying drawings.

What is claimed is:

1. A single-side backpain relieve sitting device, comprising:
    a rectangular baseplate, wherein the rectangular baseplate comprises: a first edge, a second edge, a third edge, and a fourth edge;
    a backpain relieve cushion support, wherein the backpain relieve cushion support comprises: a first side, a second side, a third side, and a fourth side, each of the four sides comprises a trapezoid shape having a bottom end and a top end, and
    a backpain relieve cushion formed at the top ends of the four sides of the backpain relieve cushion support,
    wherein the backpain relieve cushion support is removably attached to the rectangular baseplate, each of the bottom end of the four sides of the backpain relieve cushion support is aligned with a corresponding edge of the rectangular baseplate, and each top end of the four sides of the backpain relieve cushion support converges at the top end of the four sides of the backpain relieve cushion support to form the backpain relieve cushion, and the backpain relieve cushion is used to press one of two posterior superior iliac spines and to prevent counterclockwise rotary posterior pelvic tilt more than 90 degrees to a neutral and intuitive Lumbar lordotic angle while in a sitting position without compression over the spinous processes of the sacrum.

2. The single-side backpain relieve sitting device of claim 1,
    wherein the backpain relieve sitting device is removably and vertically mounted on a chair such that the first edge of the rectangular baseplate is aligned with a spine of a person sitting on the chair.

3. The single-side backpain relieve sitting device of claim 1, wherein the rectangular baseplate comprises a rigid board.

4. The single-side backpain relieve sitting device of claim 1, wherein the rectangular baseplate comprises four rounded corners.

5. The single-side backpain relieve sitting device of claim 1, wherein the rectangular baseplate is approximately six inches in height and six inches in width.

6. The single-side backpain relieve sitting device of claim 1, wherein the backpain relieve cushion comprises a pressable soft material to prevent counterclockwise rotary posterior pelvic tilt more than 90 degrees.

7. The single-side backpain relieve sitting device of claim 1, wherein each of the four sides of the backpain relieve cushion support comprises a trapezoid shape, and a depth D1 of the backpain relieve cushion support is approximately 2.0 to 6.5 inches.

8. The single-side backpain relieve sitting device of claim 1, wherein a lateral distance L1 between a center of the backpain relieve cushion and the first edge of the rectangular baseplate is approximately 1.5 to 3.0 inches.

9. The single-side backpain relieve sitting device of claim 1, wherein a vertical distance H1 between a center of the backpain relieve cushion and the fourth edge of the rectangular baseplate is approximately 3.0 to 5.0 inches.

10. The single-side backpain relieve sitting device of claim 1, wherein the backpain relieve cushion comprises a parallelogram, wherein the parallelogram is shaped to descend from the third side to the second side of the backpain relieve cushion support to accommodate variations of distance between two posterior superior iliac spines among children, adults, males and females.

11. A dual-side backpain relieve sitting device, comprising:
    a rectangular baseplate, wherein the rectangular baseplate comprises: a first edge, a second edge, a third edge, a fourth edge, and a center line between the second edge and the fourth edge;
    a pair of backpain relieve cushion supports having a first backpain relieve cushion support and a second backpain relieve cushion support, wherein the first backpain relieve cushion support comprises: a first side, a second side, a third side, and a fourth side, the second backpain relieve cushion support comprises: a first side, a second side, a third side, and a fourth side, and each of the four sides comprises a trapezoid shape having a bottom end and a top end, and
    a pair of backpain relieve cushions having a first backpain relieve cushion and a second backpain relieve cushion, wherein each of the first backpain relieve cushion of the second backpain relieve cushion is formed at the corresponding top ends of the four sides of the pair of backpain relieve cushion supports,
    wherein the pair of backpain relieve cushion supports is removably attached side-by-side to the rectangular baseplate, the bottom end of the third side of the first backpain relieve cushion support connects the bottom end of the third side of the second backpain relieve cushion support through a space along the center line to form a valley of non-contact space, each top end of the four sides of the first backpain relieve cushion support converges to form the first backpain relieve cushion, and each top end of the four sides of the second backpain relieve cushion support converges to form the second backpain relieve cushion, respectively, the pair of the backpain relieve cushions is used to press two corresponding posterior superior iliac spines and to prevent counterclockwise rotary posterior pelvic tilt more than 90 degrees to a neutral and intuitive Lumbar lordotic angle while in a sitting position without compression over the spinous processes of the sacrum.

12. The dual-side backpain relieve sitting device of claim 11, wherein the dual-side backpain relieve sitting device is removably and vertically mounted on a chair such that the center line of the rectangular baseplate is aligned with a spine of a person sitting on the chair.

13. The dual-side backpain relieve sitting device of claim 11, wherein the rectangular baseplate comprises a rigid board.

14. The dual-side backpain relieve sitting device of claim 11, wherein the rectangular baseplate comprises four rounded corners.

15. The dual-side backpain relieve sitting device of claim 11, wherein the rectangular baseplate is approximately 6 inches in height and 12 inches in width.

16. The dual-side backpain relieve sitting device of claim 11, wherein each of the pair of backpain relieve cushions comprises a pressable soft material to prevent counterclockwise rotary posterior pelvic tilt more than 90 degrees.

17. The dual-side backpain relieve sitting device of claim 11, wherein each of the four sides of the pair of backpain relieve cushions comprises a trapezoid shape, and a depth D2 of the backpain relieve cushion supports is approximately 2.0 to 6.5 inches.

18. The dual-side backpain relieve sitting device of claim 11, wherein a lateral distance L2 between a center of the first backpain relieve cushion and a center of the second backpain relieve cushion is approximately 3.0 to 5.0 inches.

19. The dual-side backpain relieve sitting device of claim 11, wherein a vertical distance H2 between a center of the first backpain relieve cushion and the third edge of the rectangular baseplate and another vertical distance H2 between a center of the second backpain relieve cushion and the third edge of the rectangular baseplate are approximately about 3.0 to 5.0 inches.

20. The dual-side backpain relieve sitting device of claim 11, wherein each of the pair of backpain relieve cushions comprises a parallelogram, wherein the parallelogram of the first backpain relieve cushion is shaped to descend from the second side towards the third side of the first backpain relieve cushion support, and the parallelogram of the second backpain relieve cushion is shaped to descend from the second side towards the third side of the second backpain relieve cushion support to accommodate variations of distance between two posterior superior iliac spines among children, adults, males and females.

\* \* \* \* \*